(12) United States Patent
Ivanov et al.

(10) Patent No.: US 10,509,006 B2
(45) Date of Patent: Dec. 17, 2019

(54) DEVICES AND METHODS FOR MEASURING THE PROPERTIES OF MACROMOLECULES

(71) Applicant: Axbio Inc., Santa Clara, CA (US)

(72) Inventors: Igor Ivanov, Santa Clara, CA (US); Albert Chueh, Santa Clara, CA (US); Licheng Niu, Santa Clara, CA (US); Hui Tian, Santa Clara, CA (US)

(73) Assignee: Axbio Inc., Santa Clara, CA (US)

( * ) Notice: Subject to any disclaimer, the term of this patent is extended or adjusted under 35 U.S.C. 154(b) by 0 days.

(21) Appl. No.: 15/628,517

(22) Filed: Jun. 20, 2017

(65) Prior Publication Data

US 2017/0363569 A1    Dec. 21, 2017

Related U.S. Application Data

(60) Provisional application No. 62/352,450, filed on Jun. 20, 2016.

(51) Int. Cl.
| | |
|---|---|
| *G01N 27/327* | (2006.01) |
| *G01N 33/50* | (2006.01) |
| *G01N 33/543* | (2006.01) |
| *B01L 3/00* | (2006.01) |
| *G01N 27/74* | (2006.01) |
| *G01N 33/487* | (2006.01) |

(52) U.S. Cl.
CPC .......... *G01N 27/3278* (2013.01); *B01L 3/502* (2013.01); *G01N 27/745* (2013.01); *G01N 33/48721* (2013.01); *G01N 33/505* (2013.01); *G01N 33/54326* (2013.01); *G01N 2800/12* (2013.01)

(58) Field of Classification Search
CPC ......... G01N 27/3278; G01N 33/48721; G01N 27/745; G01N 33/505; G01N 33/54326; B01L 3/502

See application file for complete search history.

(56) References Cited

U.S. PATENT DOCUMENTS

| | | | |
|---|---|---|---|
| 6,485,690 B1* | 11/2002 | Pfost | B01J 19/0046 422/552 |
| 7,632,470 B2* | 12/2009 | Tabata | B01J 19/0093 422/130 |
| 2009/0167288 A1 | 7/2009 | Reid et al. | |
| 2009/0267507 A1* | 10/2009 | Takashima | H01L 51/0011 313/511 |
| 2012/0024700 A1 | 2/2012 | Boccardi et al. | |
| 2012/0028845 A1 | 2/2012 | Teggatz et al. | |

(Continued)

FOREIGN PATENT DOCUMENTS

WO    2016/154302 A1    9/2016

OTHER PUBLICATIONS

Search Report for International Application No. PCT/US2017/038376, dated Sep. 19, 2017, 10 pages.

(Continued)

*Primary Examiner* — Melanie Brown

(57) ABSTRACT

Devices for use in determining properties of biochemicals and macromolecules derived from a biological sample include a fluid control unit and a macromolecule measurement unit integrated on a monolithic platform. Devices and methods of measuring the properties of macromolecules using immobilized magnetic particles are also disclosed.

10 Claims, 12 Drawing Sheets

(56) References Cited

U.S. PATENT DOCUMENTS

| | | |
|---|---|---|
| 2012/0267729 A1 | 10/2012 | Dang et al. |
| 2013/0260472 A1* | 10/2013 | Holt ................ G01N 33/48721 |
| | | 436/149 |
| 2013/0345065 A1* | 12/2013 | Hassibi ................ C12Q 1/6874 |
| | | 506/2 |
| 2014/0110259 A1 | 4/2014 | Takahashi et al. |
| 2015/0125872 A1 | 5/2015 | Chen et al. |

OTHER PUBLICATIONS

International Search Report and Written Opinion for Application No. PCT/US2017/038376, dated Nov. 9, 2017, 16 pages.
International Search Report and Written Opinion for Application No. PCT/US2018/017762, dated Jun. 7, 2018, 12 pages.
Hu, Ying et al., "Detection of Analysis of DNA Recapture Through a Solid-State Nanopore," Chinese Science Bulletin, Oct. 2014, vol. 59, No. 35, p. 4953-4959.
International Preliminary Report on Patentability for Application No. PCT/US2017/038376, dated Jan. 3, 2019, 9 pages.

* cited by examiner

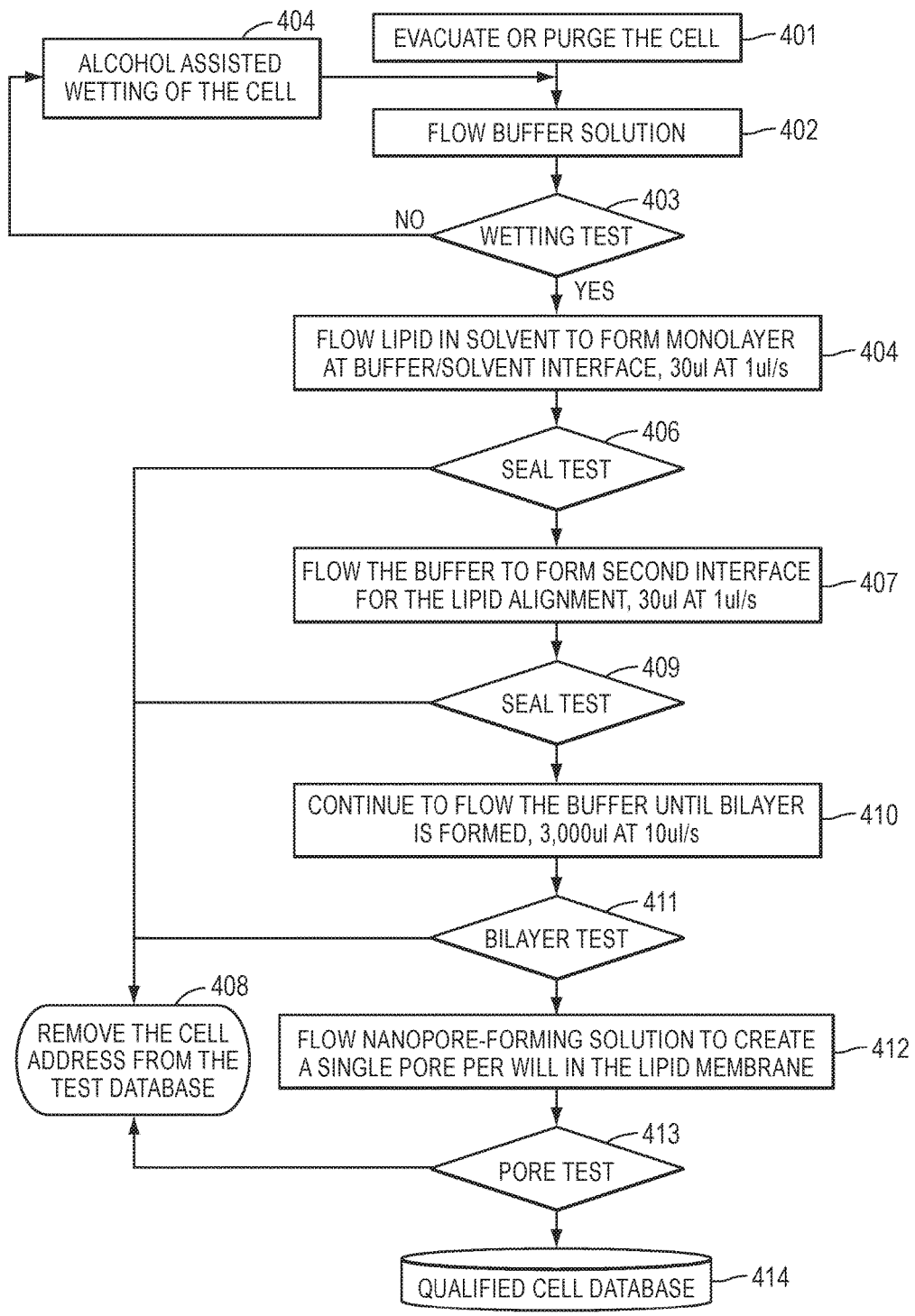

US 10,509,006 B2

DEVICES AND METHODS FOR MEASURING THE PROPERTIES OF MACROMOLECULES

This application claims the benefit under 35 U.S.C. § 119(e) of U.S. Provisional Application No. 62/352,450 filed on Jun. 20, 2016, which is incorporated by reference in its entirety.

FIELD

The present invention relates to devices and methods for determining the properties of macromolecules. The device includes a fluid control unit and a macromolecule measurement unit integrated on a monolithic platform. Devices and methods for measuring the properties of macromolecules using immobilized magnetic particles are also disclosed.

BACKGROUND

Determining the properties of biochemicals and macromolecules in a biological sample is important for medicine.

There is a need to provide versatile and robust measurements of macromolecules derived from biological samples that are simple and convenient.

SUMMARY

According to the present invention, macromolecule measurement devices comprise an electronic sensing structure; an interface structure overlying the electronic sensing structure; a macromolecule measurement structure overlying the interface structure, wherein the macromolecule measurement structure comprises a plurality of macromolecule measurement cells; and a fluid control structure overlying the macromolecule measurement structure.

According to the present invention, methods of fabricating macromolecule measurement devices comprise providing a macromolecule measurement unit, wherein the macromolecule measurement unit comprises an electronic sensing structure, an interface structure overlying the electronic sensing structure, and a macromolecule measurement structure overlying the interface structure; providing a fluid control unit wherein the fluid control unit comprises a carrier, a release layer overlying the carrier, and a fluid control structure overlying the release layer; and bonding the fluid control structure to the macromolecule measurement structure.

According to the present invention, methods of preparing a macromolecule measurement cell comprise applying a vacuum to the measurement cell, purging the measurement cell with a gas, or a combination thereof.

According to the present invention, devices for the measurement of macromolecules comprise measurement chamber, wherein the measurement chamber comprises an electrode comprising a molecule capable of interacting with a macromolecule to cause a change in an response detectable by the electrode; a reaction chamber fluidly coupled to the measurement chamber and fluidly coupled to one or more microfluidic channels; and a magnet configured to produce a magnetic field in the reaction chamber.

According to the present invention, methods for measuring macromolecules comprise introducing magnetic particles into a reaction chamber, wherein the magnetic particles comprise a molecule configured to bind cells of a biological sample to the magnetic particles; immobilizing the magnetic particles in the reaction chamber with a magnetic field; exposing the immobilized magnetic particles to the biological sample to bind the cells; washing the immobilized magnetic particles comprising the bound cells; exposing the bound cells to a chemical to produce a solution comprising a macromolecule expressed by the cell; introducing the solution comprising the expressed macromolecule into a measurement chamber; and measuring the macromolecule in the measurement chamber.

According to the present invention, methods of diagnosing tuberculosis comprise measuring interferon-γ according to methods of the present invention.

BRIEF DESCRIPTION OF THE DRAWINGS

Those skilled in the art will understand that the drawings described herein are for illustration purposes only. The drawings are not intended to limit the scope of the present disclosure.

FIG. 4 is a flow diagram showing steps in a method of preparing a macromolecule measurement cell according to the present disclosure.

FIG. 6 shows a top view of a microfluidic system for measuring macromolecules using magnetic particles according to methods provided by the present disclosure.

FIG. 7 shows the introduction provided by magnetic particles into a reaction chamber according to methods of the present disclosure.

FIG. 8 shows the introduction a biological sample into a reaction chamber containing immobilized magnetic particles according to methods provided by the present disclosure.

FIG. 9 shows the introduction of a wash buffer into a reaction chamber containing cells bound to immobilized magnetic particles according to methods provided by the present disclosure.

FIG. 10 shows the introduction of a cell stimulation chemical into a reaction chamber containing cells bound to immobilized magnetic beads according to methods provided by the present disclosure.

FIG. 11 shows the introduction of solution from the reaction chamber into the measurement chamber according to methods provided by the present disclosure.

Reference is now made to devices and methods according to the present invention. The disclosed embodiments are not intended to be limiting of the claims. To the contrary, the claims are intended to cover all alternatives, modifications, and equivalents.

DETAILED DESCRIPTION

Figure 1:
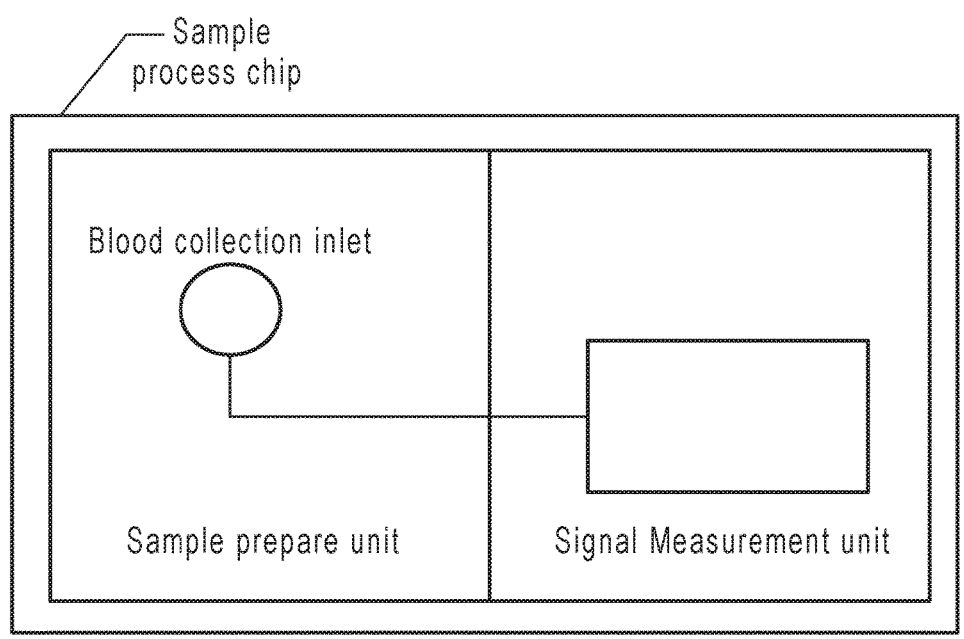
FIG. 1 shows a top view of a sample process chip including a blood collection inlet, a sample preparation unit, and a sample measurement unit.

Macromolecular measurement devices provided by the present disclosure include a sample preparation unit and a signal measurement unit integrated on a single monolithic platform. As shown in FIG. 1, a device can include a sample preparation unit that can have a collection inlet for a biological sample such as blood, and a signal measurement unit integrated onto a sample process chip.

The device can be disposable or reusable.

The sample preparation unit can be configured to collect a biological sample, to purify target biochemicals in a solution, to manipulate the concentration of the biomolecules in the solution, to adjust the temperature of the solution, to adjust the pH of the solution, to adjust the composition of the solution, and/or to adjust the pressure of the solution. The biological sample can be, for example, blood. The sample size can be, for example, less than 10 μL, less than 5 μL, or less than 2 μL. After purification, the processed sample size can be, for example, less than 10 nL, less than 1 nL, less than 100 fL, or less than 10 fL.

The signal measurement unit can comprise subunits configured to detect properties of a target biochemical, a target macromolecule, or a combination thereof. The biochemical or macromolecule can be, for example, a protein, a cytokine, an oligonucleotide such as deoxyribonucleic acid or ribonucleic acid, or a combination of any of the foregoing.

The purification process can include the use of nanoparticles with predefined properties and molecular separation based on molecular weight. Purification can include washing and the use of selective and controlled absorption.

Signal measurement methods include the use of biological, chemical, or physical signals with or without the use of additional markers.

A signal measurement unit can include subunits configured to control the motion, shape, and location of the biochemicals or macromolecules. Signal measurement can include measuring different properties of the macromolecule. Signal measurement can include using different measurement methods. The spatial resolution of a measured property can be, for example, less than 1 nm or less than 0.2 nm.

The signal detected by the signal measurement unit can be generated by electrons, protons, ions, holes, photons, phonons, or a combination of any of the foregoing.

Devices provided by the present disclosure can include a fluid control unit and a macromolecule measurement unit. A fluid control unit can include subsystems for providing macromolecules that can be measured using the measurement unit. Sample preparation can involve taking a biological sample such as a blood sample, extracting macromolecules from the biological sample, and purifying one or more macromolecules of interest. The one or more purified or concentrated macromolecules of interest can be introduced into the measurement unit. A sample preparation unit can be coupled to a macromolecular measurement device that comprises a fluid control unit a macromolecule measurement unit.

The fluid control unit and the measurement unit can be sealed to allow operation of the device within a wide range of pressure. For example, the differential pressure between the internal volumes of the device and the environment can be within a range from $10^{-7}$ Pa to 700 kPa. The ability to control the pressure can facilitate removal or elimination of gases adhering to the internal surfaces of the device. Air and/or gases can adhere to a hydrophobic surface immersed in aqueous solution or on hydrophilic surface immersed in a non-polar solvent or on hydrophobic/oligophobic surfaces immersed in a non-polar solvent to form gas bubbles. The presence of gas bubbles can adversely affect solution flow, cause the formation of layers between a solution and surfaces, and can affect the quality of electrical contact between an electrode and a solution. Oxygen can also chemically degrade the macromolecules. For example, organic materials can be susceptible to oxidation and the kinetics of certain chemical interactions such antibody-antigen binding, transcription, and de novo assembly, can be dependent on the composition and concentrations of dissolved gases. Removing oxygen can prevent oxidation of macromolecules such as nucleotides, lipids, and antibodies. Reducing the amount and content of dissolved gases can increase the shelf life of the reagents used in the device and can improve the accuracy and reproducibility of the measurements.

Prior to use, air can be removed from the internal volumes by applying a vacuum to the fluid control unit and measurement unit and subsequently purged with suitable gases to facilitate removal of residual oxygen and other gases adhering to the internal surfaces of the device. After removing residual gases from the system the internal volumes of the device can be filled with a gas such as $N_2$.

Different gases and vacuum/pressure protocols can be used to prepare the fluid control unit and the measurement unit. Because the internal sidewalls of the sample preparation unit and the measurement unit comprise different materials it can be useful to employ different gases and different pressure protocols to remove residual gases such as oxygen from the units.

Figure 2:
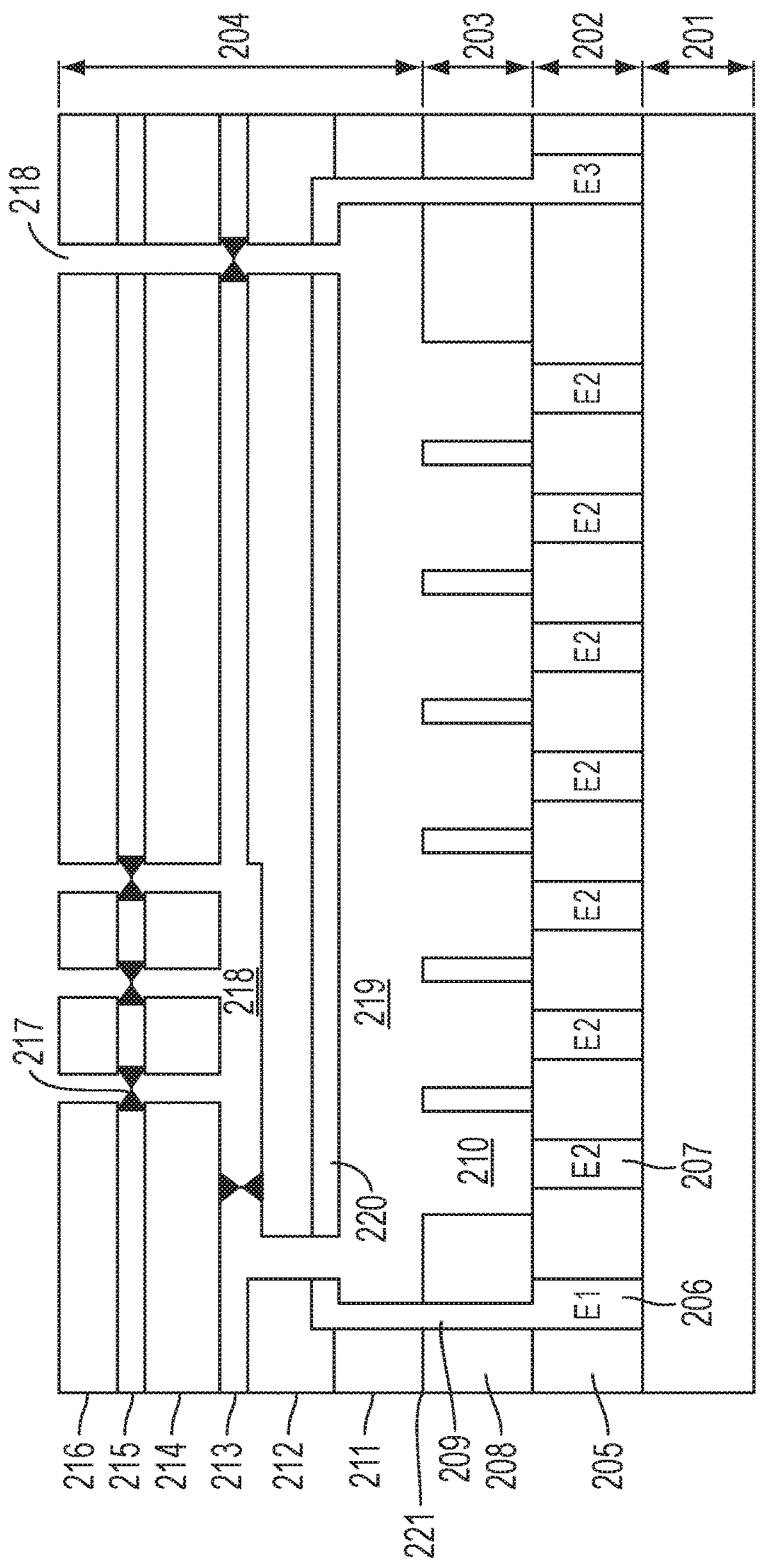
FIG. 2 shows a cross-sectional view of an example of a macromolecule measurement device according to the present disclosure.

An example of an macromolecule measurement device is shown in FIG. 2. The device includes fluid control unit 504 and a measurement unit including structures 501/502/503. The measurement unit includes an electronic sensing structure 201, which can comprise silicon CMOS electronics. An electronic interface structure 202 overlies the electronic sensing structure 201. Electronic interface structure 202 includes electrodes, such as anodes 207 and cathodes 206 separated by insulator 205 such as $SiO_2$. Anodes 207 and cathode 206 are electrically interconnected to elements of the electronic sensing structure 201. A measurement structure 203 overlies the interface structure 202 and includes insulators 208 defining individual measurement cells 210. Measurement structure 203 also includes cathode interconnects 209. Insulators 208 can comprise $SiO_2$ and can be surface treated to provide a hydrophobic surface such as a polyphosphate surface treatment on the sidewalls of the measurement cells 210.

The fluid control unit 204 can comprise structures for controlling the flow of solutions into and from the measurement cells and can be fluidly connected to an apparatus for isolating and purifying macromolecules from a biological sample for analysis using the measurement unit. As shown in FIG. 2, fluid control preparation unit 204 overlies the measurement structure 203 of the measurement unit. The fluid control unit 204 can include a plurality of layers 211-216, which can comprise fluid flow channels 216/218 and microfluidic valves 217. For example, layer 211 overlying the measurement cells 210 includes flow channel 219 fluidly coupled to each of the measurement cells 210. The lower surface of layer 213, which is in electrical contact with flow channel 219 and measurement cells 210 includes cathode 220, which is electrically interconnected to electronic sensing structure 201. Layers 211-216 can comprise polymeric materials. The configuration of layers 211-216 of the sample preparation unit 204 is for illustrations purposes only, and many configurations can be envisioned. Layers 211-216 can be configured to prepare nanopore-containing bilayers in each of the measurement cells 210, to deliver macromolecules to each of the measurement cells, to recirculate measured macromolecules, and to prepare solutions containing the macromolecules from a biological sample for measurement. The fluid control unit 204 can be fluidly coupled to reservoirs containing buffer, lipid solutions, nanopore-containing solutions, and sample reservoirs. The fluid control unit can be fluidly coupled to a sample preparation unit (not shown). Microfluidic valves 217 can be independently actuated through a controller. The controller can route solutions as appropriate, for example, to prepare nanopore-containing bilayers, prepare macromolecules for measurement, and deliver the macromolecules to measurement cells. The microfluidic layers 211-2016 can comprise siloxanes such as polydimethylsiloxanes, expoxy-based photoresists, or polyimides.

Each of the structures and layers within the fluid control unit and measurement unit can be fabricated or bonded to each of the other layers such that the device can maintain an internal pressure within a range, for example, from $1E10^{-7}$ Pa to 700 kPa, from $1E^{-5}$ Pa to 700 kPa, or from $1E^{-3}$ Pa to 700 kPa. The seal between layers 201-203 of the measurement unit can be provided using semiconductor fabrication methods such as using molecular beam epitaxy or metal-organic chemical vapor deposition. The seals between layers 201-216 of sample preparation unit 204 can be formed using semiconductor fabrication methods. The interface 221 between the fluid control structure 204 and measurement well structure 203 can be formed using polymer-to-oxide bonding methods.

The device can be fabricated on a single wafer or on two wafers that are subsequently bonded.

For example, in one method, using integrated circuit and semiconductor fabrication methods, an electronic sensing structure can be fabricated, an interface structure can be fabricated overlying the sensing structure, a measurement structure can be fabricated overlying the interface structure, and the layers of the fluid control unit can be fabricated overlying the measurement structure.

To reduce manufacturing costs the fluid control unit and the measurement unit can be fabricated using separately and subsequently bonded.

For example, the measurement unit can be fabricated by forming an electronic sensing structure, an interface structure overlying the electronic sensing structure and a measurement structure overlying the electronic sensing structure. The fluid control unit comprising the fluid control elements can be fabricated by depositing a release layer on a carrier such as a silicon wafer, and forming the fluid control layers on the release layer. The measurement and sample preparation units can be bonded and the release layer and carrier removed from the device. Using this method, different materials and methods can be used to fabricate the sample preparation unit and the measurement unit. For example, the measurement unit can be fabricated using semiconductor fabrication methods, and the fluid control unit can be fabricated using thin film lamination methods such as reel-to-reel processing. The fluid control unit can also be fabricated using semiconductor methods using photoresists. Also, for example, the measurement unit can comprise materials deposited using semiconductor fabrication methods such as semiconductor materials and inorganic insulators, and the fluid control subunit can comprise polymeric materials.

Macromolecule measurement devices provided by the present disclosure can have small dimensions. The use of small dimensions in the fluid control and measurement cells can reduce the volume of materials used to measure such as sequence macromolecules. In the devices provided by the present disclosure a measurement cell can have a cross-sectional dimension, for example, from 2 µm to 15 µm, such as from 5 µm to 10 µm. A microfluidic channel can have a cross-sectional dimension, for example from 0.5 µm to 750 µm, from 1 µm to 700 µm, from 10 µm to 600 µm, from 30 µm to 500 µm, from 0.5 µm to 50 µm, or from 0.5 µm to 100 µm.

Figure 3A:
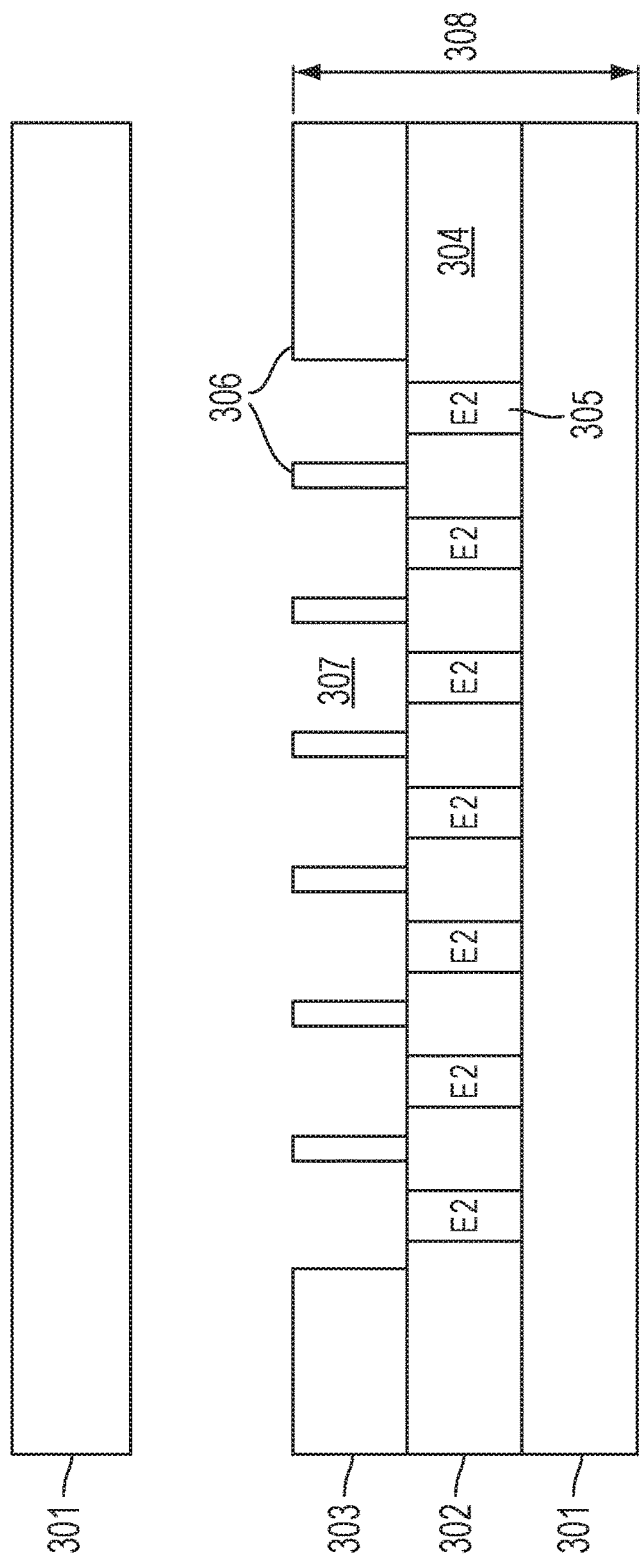
FIGS. 3A-3D show cross-sectional views of assemblies during the fabrication of a macromolecular measurement device according to the present invention.

Examples of steps and subassemblies used during the fabrication of a macromolecular measurement device provided by the present disclosure are shown in FIGS. 3A-3D. FIG. 3A shows an example of the measurement unit. Beginning with an electronic sensing structure 301 comprising, for example, silicon-CMOS electronics, an interface structure 302 is grown on the electronic sensing structure 301 and a measurement cell structure 303 is grown on interface structure 302. Electrodes 305 such as anodes in interface structure 302 electrically interconnect the measurement cells 307 in measurement cell structure 303 to the circuitry of sensing structure 301. Electrodes 305 are separated by insulators 304 and measurement cells 307 are isolated and define by insulators 306. Insulators 304 and 306 can be any suitable material such as silicon dioxide. Measurement unit 308 comprises structures 301-303.

Figure 3B:
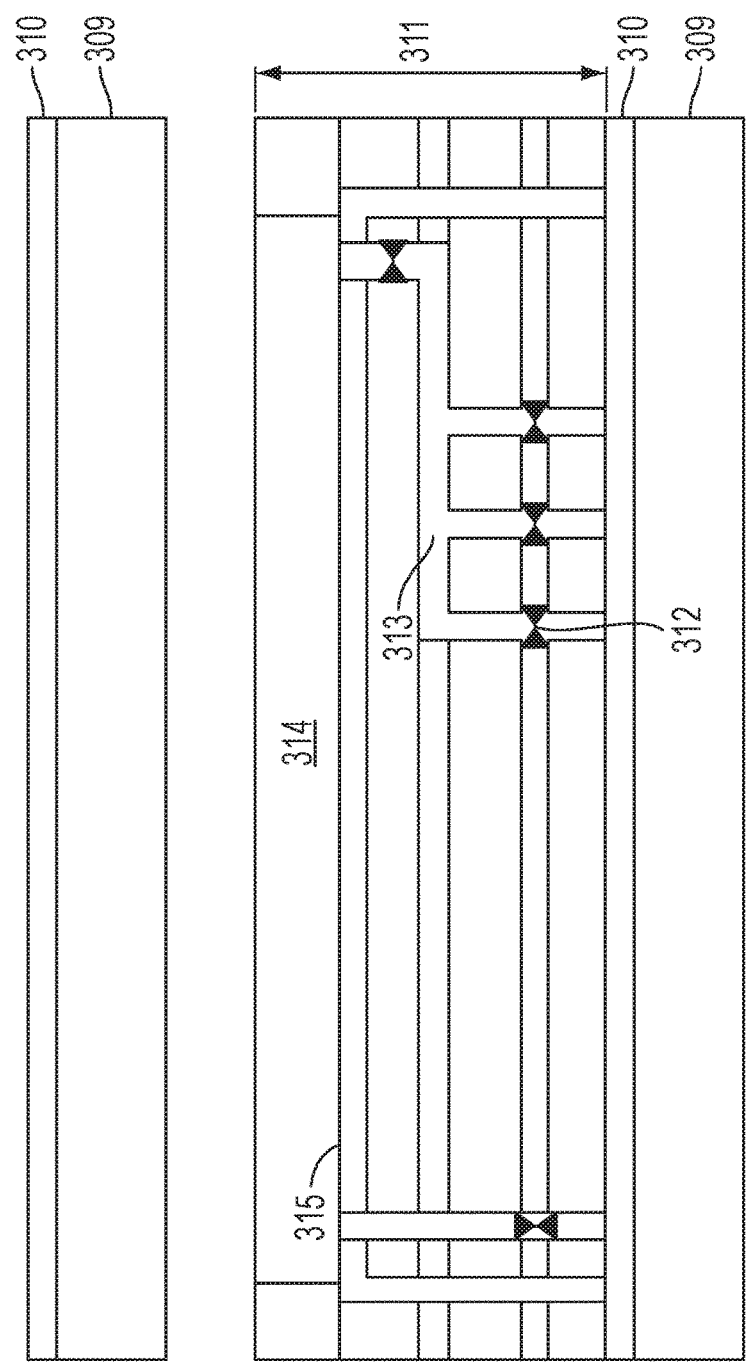

FIG. 3B shows fluid control unit 311. The microfluidic layers of fluid control unit 311 can be fabricated using any suitable method, such as photolithography. The microfluidic layers can be fabricated on a release layer 310 on a carrier 309.

Figure 3C:
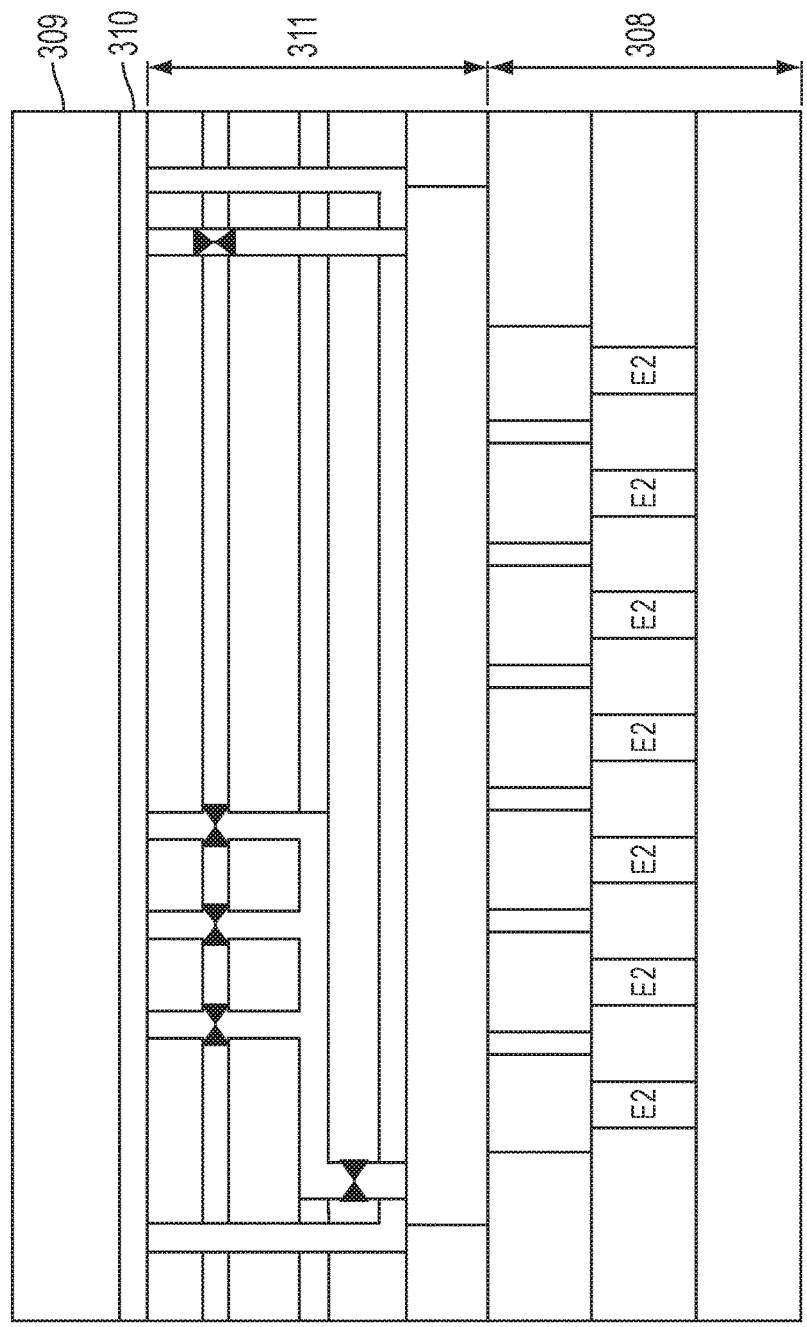

FIG. 3C shows a macromolecule measurement unit after the fluid control unit 311 and the measurement unit 308 have been bonded together with the fluid control unit 311 remaining attached to release layer 310 and carrier 309.

Figure 3D:
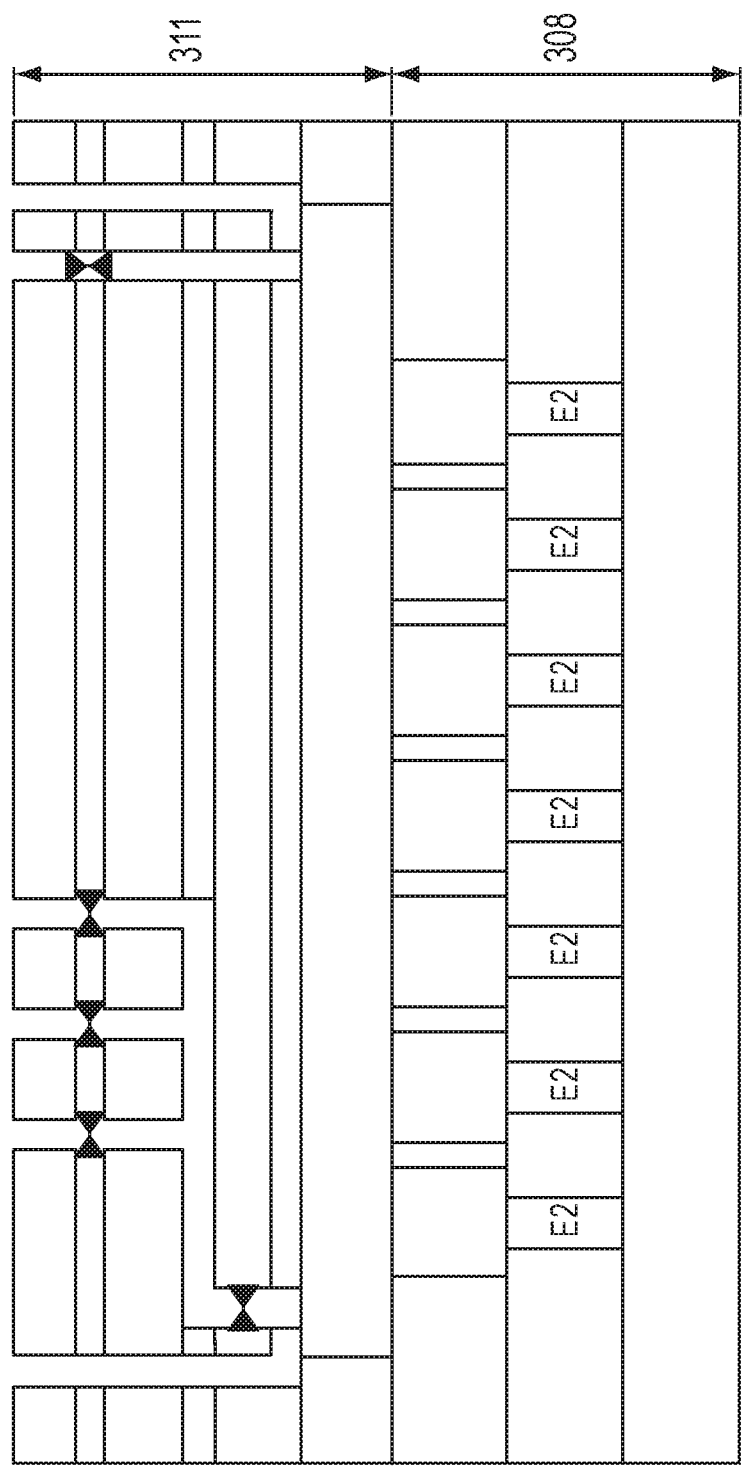

FIG. 3D shows a macromolecule measurement device after the release layer and carrier have been removed from the fluid control unit 311. The macromolecule measurement device shown in FIG. 3D includes fluid control unit 311 and measurement unit 308.

For a measurement device to be useful for macromolecular sequences nanopore-containing bilayer can be assembled in the measurement cells. An example of a method for forming a nanopore-containing lipid bilayer in the measurement cells is outlined in the flow chart presented in FIG. 4 and in the cross-sectional illustrations shown in FIGS. 5A-5F.

Figure 5A:
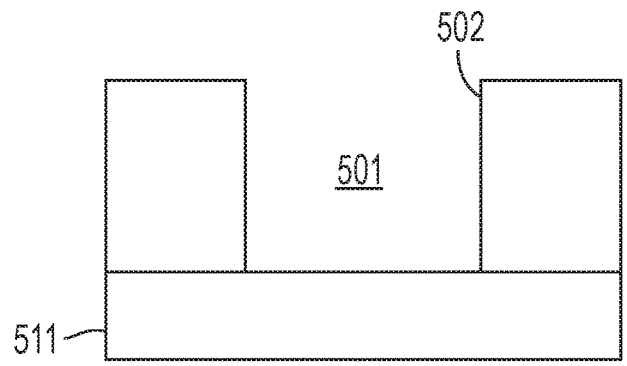
FIGS. 5A-5F show cross-sectional views of a macromolecule measurement cell during preparation of the nanopore-containing lipid bilayer.

A macromolecule measurement device such as the device shown in FIG. 2 is first provided. FIG. 5A shows a cross-section of a measurement cell 501 with sidewalls 502 overlying interface structure 511. An electrode such as an anode (not shown) extends through interface structure 511 and electrically interconnects measurement cell 501 with an electronic sensing structure (not shown).

Figure 5B:
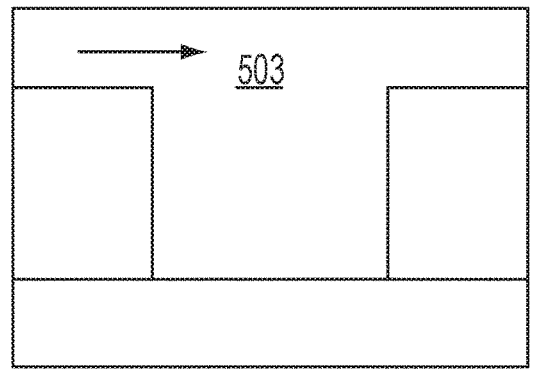
Figure 5C:
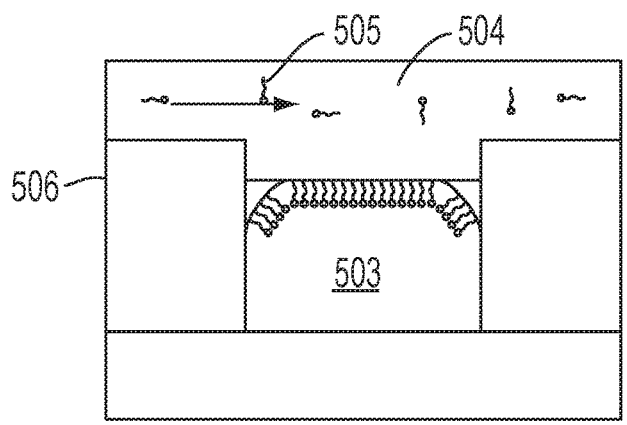
Figure 5D:
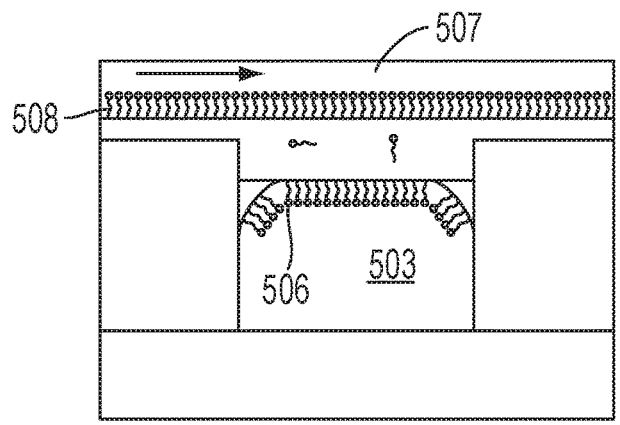
Figure 5E:
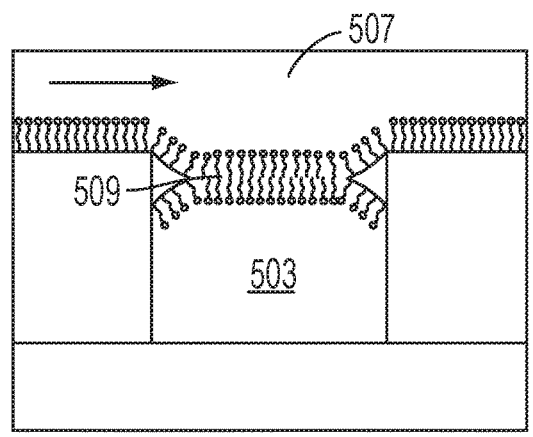

Gases are then removed from the measurement cells by applying a vacuum and/or by purging the cells with a suitable gas such as $N_2$ (401, 501). A degassed buffer solution is then passed through the cells (402, 502). The degassed buffer solution can be prepared by applying a low vacuum to the buffer solution such as within a range from 0.5 Torr to 5 Torr (66.6 Pa to 667 Pa). A wetting test is then performed, for example, by measuring the ratio of pressure to flow rate within a channel and/or by visually inspecting the flow channels. If the surfaces of the cells are sufficiently wetted, then subsequent processing can proceed. If wetting is not sufficient (404), then an alcoholic solvent is passed through the system and the buffer flow step (403) is repeated until the surfaces are sufficiently wetted. Surface wetting can be measured using ratio of liquid flow rate and pump pressure or by detection of gas bubbles using optical microscopy or photodetector. A surface is consider to be sufficiently wetted when_ratio of liquid flow rate to vacuum pressure corresponds to pre-calibrated value and/or no bubbles are detected by optical methods. After the cell surface is wetted, a lipid bilayer can be assembled in the cell. First, as shown in FIG. 5B, a buffer solution is flowed through the cell A flow of solvent containing a lipid preparation is then passed through the system (405, 503), to form a lipid monolayer at the interface between the buffer within the well and the lipid-containing solvent. For example, FIG. 5C shows a measurement cell containing buffer 503 and a solution 504 containing lipids 505 separated by a lipid monolayer 506. The flow volume can be, for example, 30 µL and the flow rate can be, for example 1 µL/sec. To evaluate the integrity of the lipid monolayer a seal test 406 can be performed by applying a potential between two coplanar electrodes, for example, electrodes between adjacent cells, and measuring the resulting current. The integrity of the lipid monolayer is considered adequate when the leakage current is less than 1 pA. After forming the lipid monolayer, a flow of a second buffer is passed through the system to form a second interface for formation of a lipid bilayer (407, 504). FIG. 5D shows a measurement cell with a buffer 503, a lipid-containing solvent 504, and second buffer 507. A first lipid monolayer 506 separates buffer 503 and lipid-containing solvent 504, and as second lipid monolayer 508 spontaneously forms at the interface between lipid-containing solvent 504 and the second buffer 507. A seal test 409 can be performed by monitoring the current between the anode and cathode for each cell. Again, the flow volume can be, for example, 30 µL and the flow rate can be, for example 1 µL/sec. The flow of the second buffer is continued until a bilayer is formed (410, 505). During formation of the lipid bilayer the flow of the second buffer can be increased, for example, to a volume of 2,000 µL at a rate of 10 µL/sec to displace the lipid-consigning solvent and cause the first and second lipid bilayers to coalesce as shown in FIG. 5E. While the second buffer is flowing through the system, the formation of the bilayer can be monitored by measuring the current between electrodes placed on the cis and trans sides of the bilayer 409. A bilayer is considered to be formed when the current is below 1 pA. A final bilayer test can be performed (411). A bilayer is considered to be of sufficient quality when the breakdown current is below 2 pA.

If the at any point in the bilayer assembly process (405-411) a cell does not pass a seal test or the bilayer test, the cell address is identified and data obtained from the identified cell is not evaluated (408).

Figure 5F:
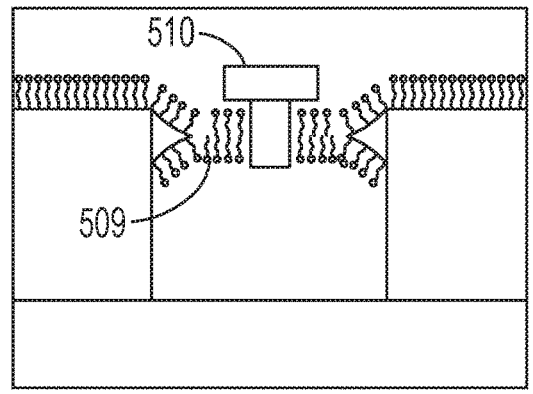

After the lipid bilayer is formed in a cell, a nanopore is then incorporated into the lipid bilayer by flowing a solution comprising nanopores through the system (412) to provide measurement cells comprising a single nanopore incorporated into the lipid bilayer. FIG. 5F shows a nanopore 510 incorporated into lipid bilayer 509. The integrity of the nanopore-containing lipid bilayer is measured by measuring the current across the bilayer and is considered to be of sufficient quality when current reaches a predetermined value established by recalibrating the system, which depends of type of nanopore, the conductivity of the electrolyte, and conditions of the electrode surfaces (413). Again, if the quality of the nanopore-containing bilayer is not acceptable, the address of the particular cell is identified and not analyzed (408).

The cells passing the nanopore test are included in the analysis database.

After the nanopore-containing bilayers are assembled in the measurement cells, the device is ready for nanopore sequencing of macromolecules (414).

Aspects of the present invention include apparatus and methods of preparing and isolating macromolecules using magnetic beads. The apparatus and methods can be used in conjunction with a measurement device provided by the present disclosure or in an independent process. The methods are illustrated in FIGS. 6-11.

Figure 6:
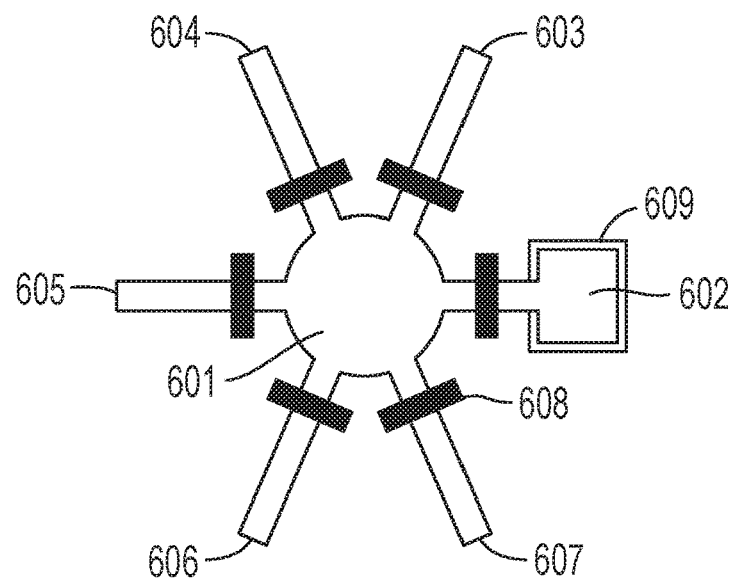
FIGS. 6-11 illustrate steps during measurement of macromolecules using immobilized magnetic particles according to methods provided by the present disclosure.

FIG. 6 shows a schematic of microfluidic system comprising a reaction chamber 601 fluidly coupled to microfluidic channels 603-607 and to detection chamber 609. Each of microfluidic channels 603-607 is fluidly coupled to a respective reservoir comprising magnetic beads (603), wash buffer (604), sample (605), and chemical 607, or to an outlet waste chamber 606. Each of the channels 603-607 and measurement chamber 609 is independently controllable using a respective microfluidic valve 608. Measurement chamber 609 can include an electrode and/or array detector coated with an antibody or aptamer capable of interacting with a macromolecule of interest. The macromolecule of interest can be, for example, a component of a biological sample, such as a blood sample.

Figure 7:
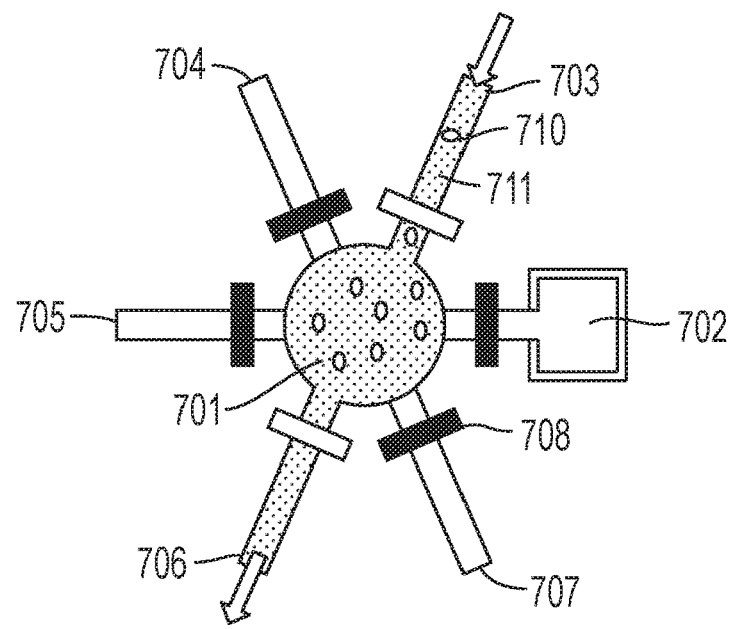

To begin the measurement process, as shown in FIG. 7, a solution 711 containing magnetic particles 710 is introduced through microfluidic channel 703 into reaction chamber 701 and through waste channel 706. A magnetic field is applied to the reaction chamber to capture and immobilize he magnetic particles in the reaction chamber. The magnetic particles can have a diameter, for example from 1 µm to 40 µm such as from 10 µm to 30 µm, or any other suitable dimension. The magnetic particles can comprise molecules capable of binding to a macromolecule of interest. For example, the magnetic particles can comprise an antibody and/or an aptamer. For example, an antibody or aptamer can be selected to bind to a macromolecule of interest in the sample, or to a cell of interest in the sample.

Figure 8:
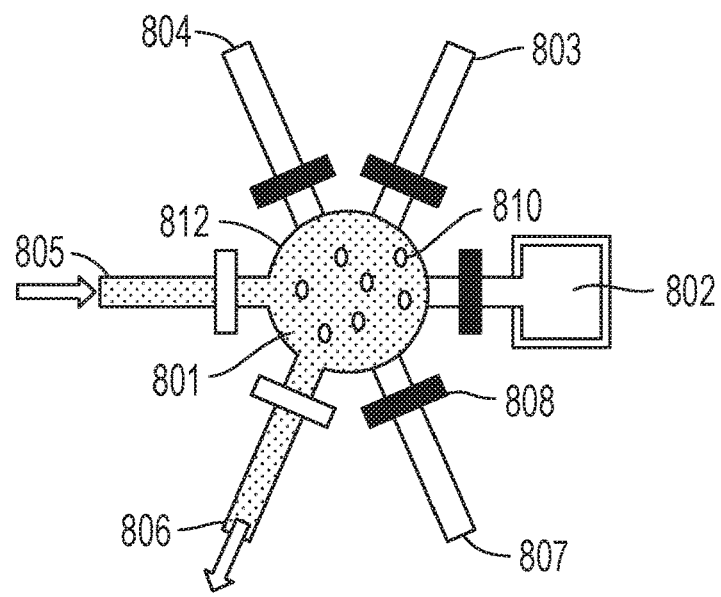

As shown in FIG. 8, after the magnetic particles are immobilized in the reaction chamber, the sample can be introduced into the reaction chamber. Sample 812 is introduced from the sample microfluidic channel 805 into reaction chamber 801 and through outlet channel 806. The volume of sample, such as a blood sample, introduced through the reaction chamber 801 can be, for example from 0.05 µL to 5 µL, such as from 1 µL to 3 µL, or any other suitable volume. A macromolecule of interest in the sample can interact with such as bind to a molecule bound to the surface of the magnetic particles. The sample can comprise cells and cells of interest can bind to molecules conjugated to the particles.

Figure 9:
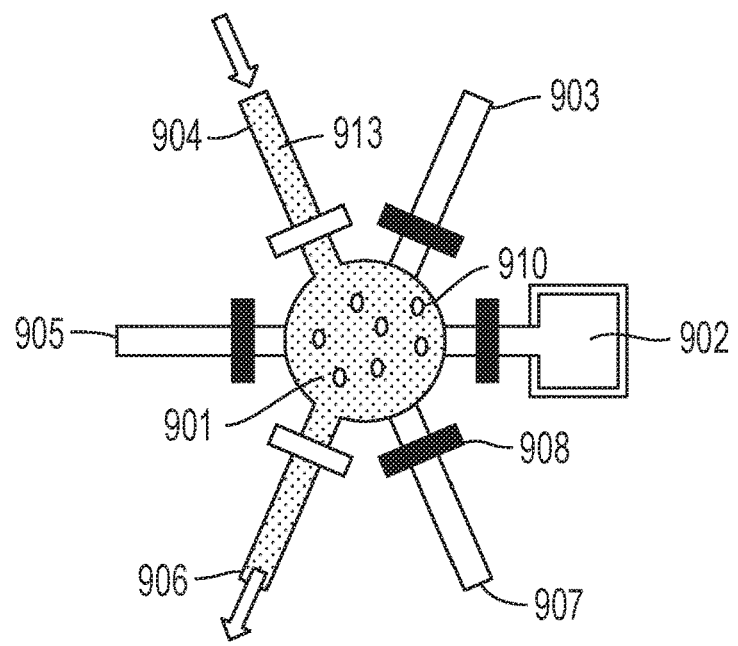
Figure 10:
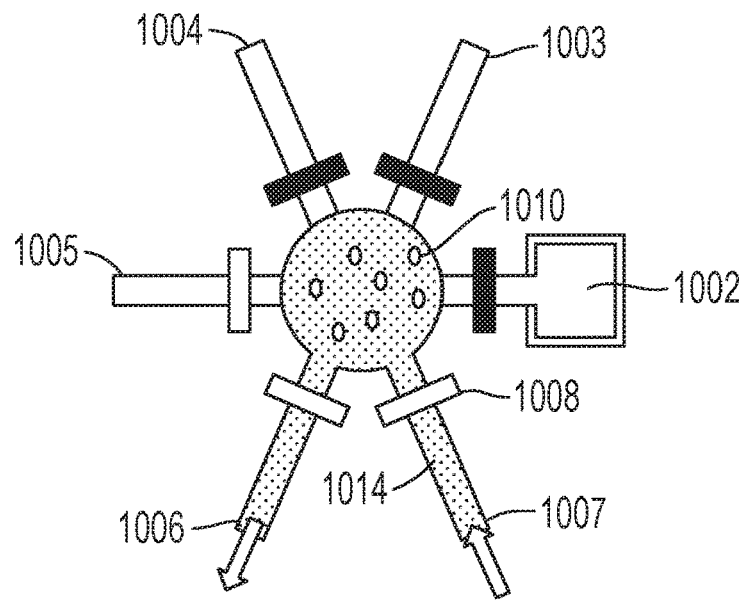

As shown in FIG. 9, after the macromolecule or cell in the sample becomes bound to the magnetic particles, the sample can be removed from the reaction chamber 901 by washing the reaction chamber 901 with a buffer 913 through microfluidic channel 904 into the reaction chamber 901 and through the outlet 906. The wash buffer removes the sample and any unbound materials.

At this point, the reaction chamber comprises macromolecules or cells bound to immobilized magnetic particles.

Adsorbed macromolecules can be released from the surface typically through oxidation of bonding functional groups using chemical reagents, changing pH, or using sonication process.

Intracellular contents can be interrogated by inducing the cells to release or secrete intracellular compounds. For example, macrophages and activated T-cells can release cytokines such as interleukins. To induce secretion of a macromolecule of interest from the immobilized cells in the reaction chamber, a chemical can be introduced into the reaction chamber that stimulates secretion of the macromolecule of interest. For example, referring to FIG. 10, the cell stimulation chemical phorbol myristate acetate (PMA) can be introduced into reaction chamber 1001 from microfluidic channel 1014. All microfluidic valves 1108 are then closed, and the cells are allowed to incubate in the presence of the cell stimulation chemical.

Figure 11:
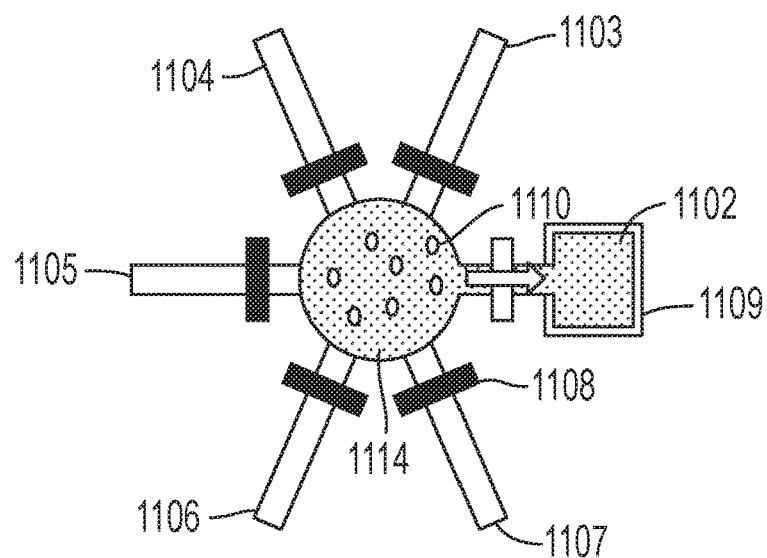

After the cells interact with the cell stimulation chemical, the solution within the reaction chamber can comprise the macromolecule of interest. As shown in FIG. 11, with the magnetic beads 1110 and bound cells remaining immobilized, the microfluidic valve 1108 that otherwise isolates the reaction chamber from the detection chamber can be opened thereby allowing the macromolecules of interest to flow into the measurement chamber 1109. The macromolecules in the measurement chamber can interact with a molecule bound to the electrode 1109 to produce a detectable electronic response. For example, for the detection of tuberculosis the magnetic particles can be conjugated with $CD^{4+}$ antibodies. $CD^{4+}$ antibodies can bind T-cells. PMA induces T cells to secrete interferon-$\gamma$ (IFN-$\gamma$), which is a marker for tuberculosis.

For example, it is known that T-cells in patients having tuberculosis produce interferon-$\gamma$. To detect tuberculosis using a system provided by the present disclosure, the detector can comprise IFN-$\gamma$ antibodies bound to an electrode. The sample can comprises blood from a patient. The magnetic particles can comprise conjugated $CD^{4+}$ antibody capable of binding T-cells. T-cells captured by the $CD^{4+}$ antibody can be stimulated to secrete interferon-$\gamma$ by exposing the T-cells to PMA. Interferon-$\gamma$ than binds to the IFN-$\gamma$ antibody to produce a measurable change in the potential of the electrode.

It can be appreciated that other macromolecules can be measured using similar techniques.

ASPECTS OF THE INVENTION

Aspect 1a. A device comprising: a sample preparation unit; and a signal measurement unit Aspect 2a. The device of aspect 1a, wherein the sample preparation unit comprises subunits configured to collect a biological sample, to purify target biochemical, to manipulate a concentration of the biochemical in a media, to adjust the temperature of the media, to adjust the pH of the media, to manipulate a composition of the media, to adjust the pressure, or a combination of any of the foregoing.

Aspect 3a. The device of any one of aspects 1a to 2a, wherein the biological sample comprises blood.

Aspect 4a. The device of any one of aspects 1a to 3a, wherein the biochemical comprises a protein, a cytokine, DNA, RNA, or a combination of any of the foregoing.

Aspect 5a. The device of any one of aspects 1a to 4a, wherein purifying comprises using nanoparticles characterized by a predefined property and using molecular weight separation.

Aspect 6a. The device of any one of aspects 1a to 5a, wherein purifying comprises washing, selective adsorption, controlled adsorption, or a combination of any of the foregoing.

Aspect 7a. The device of any one of aspects 1a to 6a, wherein the signal measurement unit comprises subunits configured to detect biological signals, chemical signals, physical signals, or a combination of any of the foregoing.

Aspect 8a. The device of any one of aspects 1a to 7a, wherein the signal measurement unit comprises a measurement subunit characterized by a spatial resolution less than 1 nm.

Aspect 9a. The device of any one of aspects 1a to 8a, wherein signal measurement unit comprises a subunit configured to detect electrons, protons, ions, holes, photons, phonons, or a combination of any of the foregoing.

Aspect 10a. The device of any one of aspects 1a to 9a, wherein the sample preparation unit and the signal measurement unit are integrated on a monolithic platform.

Aspect 11a. A method of measuring a property of a macromolecule comprising: providing the device of any one of aspects 1 to 10; depositing a biological sample onto an inlet of the sample preparation unit; preparing the biological sample; and measuring a property of a macromolecule in the biological sample using the signal measurement unit.

Aspect 1. A macromolecule measurement device, comprising: an electronic sensing structure; an interface structure overlying the electronic sensing structure; a macromolecule measurement structure overlying the interface structure, wherein the macromolecule measurement structure comprises a plurality of macromolecule measurement cells; and a fluid control structure overlying the macromolecule measurement structure.

Aspect 2. The macromolecule measurement device of aspect 1, wherein the electronic sensing structure comprises silicon-CMOS electronics.

Aspect 3. The macromolecule measurement device of any one of aspects 1 to 2, wherein, the interface structure comprises electrodes; and each of the electrodes interconnects a macromolecule measurement cell to the electronic sensing structure.

Aspect 4. The macromolecule measurement device of any one of aspects 1 to 3, wherein the macromolecule measurement structure comprises one or more flow channels fluidly coupled to each of the plurality of macromolecule measurement cells.

Aspect 5. The macromolecule measurement device of any one of aspects 1 to 4, wherein the macromolecule measurement structure comprises a cathode, wherein the cathode is electrically connected to each of the plurality of macromolecule measurement cells and to the electronic sensing structure.

Aspect 6. The macromolecule measurement device of any one of aspects 1 to 5, wherein, the fluid control structure comprises a plurality of channels and a plurality of valves; and the plurality of channels and the plurality of valves is configured to direct gas, fluid, membrane components, and/or macromolecules to and from the plurality of macromolecule measurement cells.

Aspect 7. The macromolecule measurement device of any one of aspects 1 to 6, comprising a plurality of reservoirs fluidly connected to the fluid control structure.

Aspect 8. The macromolecule measurement device of any one of aspects 1 to 7, wherein each of the electronic sensing structure, the interface structure, the macromolecule measurement structure, and the fluid control structure are sealed from the external environment within an internal pressure range from $1E10^{-7}$ Pa to 700 kPa.

Aspect 9. A method of fabricating a macromolecule measurement device, comprising: providing a macromolecule measurement unit, wherein the macromolecule measurement unit comprises an electronic sensing structure, an interface structure overlying the electronic sensing structure, and a macromolecule measurement structure overlying the interface structure; providing a fluid control unit wherein the fluid control unit comprises a carrier, a release layer overlying the carrier, and a fluid control structure overlying the release layer; and bonding the fluid control structure to the macromolecule measurement structure.

Aspect 10. The method of aspect 9, comprising, after bonding, removing the carrier and the release layer from the fluid control structure.

Aspect 11. The method of any one of aspects 9 to 10, wherein the macromolecule measurement unit is fabricated using semiconductor processing methods.

Aspect 12. The method of any one of aspects 9 to 11, wherein the flow control unit is fabricated using thin film processing and assembly methods.

Aspect 13. The method of any one of aspects 9 to 12, wherein bonding comprises polymer to oxide bonding Aspect 14. The method of any one of aspects 9 to 13, wherein the macromolecule measurement unit is fabricated by steps comprising: fabricating an electronic sensing structure; fabricating an interface structure on the electronic sensing structure; and fabricating a macromolecule measurement structure on the interface structure.

Aspect 15. The method of any one of aspects 9 to 14, wherein the fluid control unit is fabricated by steps comprising: providing a carrier; depositing a release layer onto the carrier; and fabricating a fluid control structure on the release layer.

Aspect 16. A method of preparing a macromolecule measurement cell, comprising applying a vacuum to the measurement cell, purging the measurement cell with a gas, or a combination thereof.

Aspect 17. The method of aspect 16, wherein preparing the macromolecule measurement cell comprises removing oxygen from the measurement cell.

Aspect 18. The method of any one of aspects 16 to 17, wherein the vacuum pressure is within a range from $1E10^{-7}$ Pa to 0 Pa.

Aspect 19. The method of any one of aspects 16 to 18, wherein the gas is nitrogen ($N_2$).

Aspect 20. The method of any one of aspects 16 to 19, wherein the hydrophilic solvent comprises an alcohol.

Aspect 21. The method of any one of aspects 16 to 20, further comprising forming a nanopore-containing bilayer in the measurement cell.

Aspect 22. A device for the measurement of a macromolecule, comprising: a measurement chamber, wherein the measurement chamber comprises an electrode comprising a molecule capable of interacting with a macromolecule to cause a change in an response detectable by the electrode; a reaction chamber fluidly coupled to the measurement chamber and fluidly coupled to one or more microfluidic channels; and a magnet configured to produce a magnetic field in the reaction chamber.

Aspect 23. The device of aspect 22, wherein the magnet comprises an electromagnet.

Aspect 24. The device of any one of aspects 22 to 23, wherein the one or more microfluidic channels comprises a channel for flowing magnetic particles into the reaction chamber, a channel for flowing buffer into the reaction chamber, a channel for flowing a sample into the reaction chamber, and an outlet for flowing fluid from the reaction chamber.

Aspect 25. The device of aspect 24, wherein the one or more microfluidic channels comprises a channel for flowing a chemical into the reaction chamber.

Aspect 26. The device of any one of aspects 22 to 25, wherein each of the one or more microfluidic channels comprises an independently controllable microfluidic valve.

Aspect 27. A method for measuring a macromolecule, comprising: introducing magnetic particles into a reaction chamber, wherein the magnetic particles comprise a molecule configured to bind cells of a biological sample to the magnetic particles; immobilizing the magnetic particles in the reaction chamber with a magnetic field; exposing the immobilized magnetic particles to the biological sample to bind the cells; washing the immobilized magnetic particles comprising the bound cells; exposing the bound cells to a chemical to produce a solution comprising a macromolecule expressed by the cell; introducing the solution comprising the expressed macromolecule into a measurement chamber; and measuring the macromolecule in the measurement chamber.

Aspect 28. The method of aspect 27, wherein the molecule configured to bind the cell comprises an antibody, an aptamer, or a combination thereof.

Aspect 29. The method of any one of aspects 27 to 28, wherein the molecule configured to bind the cell is conjugated to the magnetic particle.

Aspect 30. The method of any one of aspects 27 to 29, wherein the molecule configured to bind the cell comprises a $CR^{4+}$ antibody.

Aspect 31. The method of any one of aspects 27 to 30, wherein the cell comprises a T-cell.

Aspect 32. The method of any one of aspects 27 to 31, wherein the magnetic particles comprise a diameter from 1 μm to 40 μm.

Aspect 33. The method of any one of aspects 27 to 32, wherein the biological sample comprises blood.

Aspect 34. The method of any one of aspects 27 to 33, wherein the biological sample comprises a volume from 0.1 μL to 5 μL.

Aspect 35. The method of any one of aspects 27 to 34, wherein the chemical comprises a chemical that stimulates secretion of the macromolecule from the cells.

Aspect 36. The method of any one of aspects 27 to 35, wherein the chemical stimulates secretion of interferon-γ from the cells.

Aspect 37. The method of any one of aspects 27 to 36, wherein the measurement chamber comprises an electrode comprising a molecule configured to interact with the macromolecule.

Aspect 38. The method of any one of aspects 27 to 37, wherein the molecule configured to interact with the macromolecule comprises an antibody, an aptamer, or a combination thereof.

Aspect 39. The method of any one of aspects 27 to 38, wherein, the biological sample is blood; the cell is a T-cell; the molecule configured to bind the cells is a $CD^{4+}$ antibody; the chemical is phorbol myristate acetate; the measurement chamber comprises an electrode comprising an interferon-γ antibody; and the macromolecule comprises interferon-γ.

Aspect 40 A method of diagnosing tuberculosis comprising measuring interferon-γ using the method of aspect 39.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled to their full scope and equivalents thereof.

What is claimed is:

1. A macromolecule measurement device, comprising:
   an electronic sensing structure;
   an interface structure overlying the electronic sensing structure;
   a macromolecule measurement structure overlying the interface structure, wherein the macromolecule measurement structure comprises a plurality of macromolecule measurement cells; and a fluid control structure overlying the macromolecule measurement structure, wherein each of the electronic sensing structure, the interface structure, the macromolecule measurement structure, and the fluid control structure are sealed from the external environment using semiconductor fabrication methods such that internal volumes of the device can maintain a vacuum to $1E10^{-7}$ Pa.

2. The macromolecule measurement device of claim 1, wherein the electronic sensing structure comprises silicon-CMOS electronics.

3. The macromolecule measurement device of claim 1, wherein, the interface structure comprises electrodes; and each of the electrodes interconnects a macromolecule measurement cell to the electronic sensing structure.

4. The macromolecule measurement device of claim 1, wherein the macromolecule measurement structure comprises one or more flow channels fluidly coupled to each of the plurality of macromolecule measurement cells.

5. The macromolecule measurement device of claim 1, wherein the macromolecule measurement structure comprises a cathode, wherein the cathode is electrically connected to each of the plurality of macromolecule measurement cells and to the electronic sensing structure.

6. The macromolecule measurement device of claim 1, wherein, the fluid control structure comprises a plurality of channels and a plurality of valves; and the plurality of channels and the plurality of valves is configured to direct gas, fluid, membrane components, and/or macromolecules to and from the plurality of macromolecule measurement cells.

7. A method of fabricating a macromolecule measurement device, comprising:

providing a macromolecule measurement unit, wherein the macromolecule measurement unit comprises an electronic sensing structure, an interface structure overlying the electronic sensing structure, and a macromolecule measurement structure overlying the interface structure;

providing a fluid control unit wherein the fluid control unit comprises a carrier, a release layer overlying the carrier, and a fluid control structure overlying the release layer; and bonding the fluid control structure to the macromolecule measurement structure wherein each of the electronic sensing structure, the interface structure, the macromolecule measurement structure, and the fluid control structure are sealed from the external environment using semiconductor fabrication methods such that internal volumes of the device can maintain a vacuum to $1E10^{-7}$ Pa.

8. The method of claim 7, comprising, after bonding, removing the carrier and the release layer from the fluid control structure.

9. The method of claim 7, wherein the macromolecule measurement unit is fabricated by steps comprising:

fabricating an electronic sensing structure;

fabricating an interface structure on the electronic sensing structure; and fabricating a macromolecule measurement structure on the interface structure.

10. The method of claim 7, wherein the fluid control unit is fabricated by steps comprising:

providing a carrier;

depositing a release layer onto the carrier; and fabricating a fluid control structure on the release layer.

* * * * *